United States Patent
Ross et al.

(10) Patent No.: US 6,271,205 B1
(45) Date of Patent: Aug. 7, 2001

(54) CANCER TREATMENT BY EXPRESSION OF DIFFERENTIATION FACTOR RECEPTOR

(75) Inventors: Alonzo H. Ross, Shrewsbury; Lawrence D. Recht, Holden; Mahesh B. Lachyankar, Shrewsbury, all of MA (US)

(73) Assignees: University of Massachusetts Medical Center, Worcester; Worcester Foundation for Biomedical Research, Shrewsbury, both of MA (US)

( * ) Notice: Subject to any disclaimer, the term of this patent is extended or adjusted under 35 U.S.C. 154(b) by 0 days.

(21) Appl. No.: 08/815,795

(22) Filed: Mar. 12, 1997

Related U.S. Application Data

(63) Continuation-in-part of application No. 08/310,287, filed on Sep. 21, 1994, now Pat. No. 5,789,187.
(60) Provisional application No. 60/014,466, filed on Mar. 21, 1996.

(51) Int. Cl.[7] .......................... A61K 31/711; C12N 15/63
(52) U.S. Cl. ........................................... 514/44; 435/320.1
(58) Field of Search .............................. 435/320.1, 172.1, 435/455; 424/93.2, 93.6, 93.21; 514/44

(56) References Cited

PUBLICATIONS

Redemann et al., Mol. Cell. Biol., vol. 12, No. 2, pp. 491–498 Feb. 1992.*
Orkin et al., "Report and Recommendations of the Panel to Access the NIH Investment in Research on Gene Therapy", Dec. 7, 1995.*
R. Klein et al., "The trkProto–Oncogene Encodes a Receptor for Nerve Growth Factor". Cellvol. 65, 189–197, Apr. 5, 1991.
L. Ridder et al., "Invasiveness of Primary and Secondary Brain Tumors in Vitro Correlated with Clinical Results" Neurosurgery, vol. 31, No. 6, Dec. 1992.
T. Suzuki et al., "Lack of High–Affinity Nerve Growth Factor Receptors In Aggressive Neuroblastomas", Journal of the National Cancer Institute, vol. 85, No. 5, Mar. 3, 1993.
T. Fujiwara et al., "A Retroviral Wild–type p53Expression Vector Penetrates Human Lung Cancer Spheroids and inhibits Growth by Inducing Apoptosis", Cancer Research, 53, 4129–4133, Sep. 15, 1993.
B. Hempstead et al., "Expression of Functional Nerve Growth Factor Receptors After Gene Transfer", Science, vol. 243, Jan. 1989.
H. Matsushima and E. Bogenmann, "Expression of trkA cDNA in Neuroblastomas Mediates Differentiation In Vitro and In Vivo", Molecular and Cellular biology, Dec. 1993, p. 7447–7456.
A. Obermeier et al., "Tyrosine 785 is a Major Determinant of TrK—substrate interaction", The EMBO Journal, vol. 12, No. 3, pp 933–941, 1993.
Dikic et al., "PC12 Cells Overexpressing the Insulin Receptor Undergo Insulin–Department Neuronal Differentiation", Current Biology, 1994, vol. 4 No. 8, pp 704–708.
S. Traverse et al., "EGF Triggers Neuronal Differentiation of PC12 Cells That Overexpress the EGF Receptor" Current Biology 1994, vol. 4, No. 8, pp 694–708.
G. Rovelli et al., "Chimeric Tumor Necrosis Factor–TrkA Receptors Reveal That Ligand–Dependent Activation of the TrkA Tyrosine Kinase is Sufficient for Differentiation and Survival of PC12 Cells", Proc. Natl. Acad. Sci. USA, vol. 90, pp 8717–8721, Sep. 1993.
D. Kaplan et al., "The trkProto–Oncogene Product: A Signal Transducing Receptor for Nerve Growth Factor", Science, vol. 252, pp 554–558.
B. Hempstead et al., "Overexpression of the trk Tyrosine Kinase Rapidly Accelerates Nerve Growth Factor–Induced Differentiation", Neuronpp 883–896, 1992.
C. Reynolds at al., Biological Classification of Cell Lines Derived From Human Extra–Cranial Neural Tumors, Advances in Neuroblastoma Research 2, pp 291–306, 1988.

\* cited by examiner

*Primary Examiner*—David Guzo
(74) *Attorney, Agent, or Firm*—Fish & Richardson P.C.

(57) ABSTRACT

Disclosed are methods of reducing or inhibiting the motility and/or proliferative abilities of a neural tumor cell, or of enhancing apoptosis or differentiation of the tumor cell, in which a vector comprising a nucleic acid encoding a cytoplasmic domain of a neurotrophin receptor tyrosine kinase, is transferred to the tumor cell such that the nucleic acid is expressed. The methods of the invention result in reduced tumorigenicity of neural tumors.

11 Claims, 6 Drawing Sheets

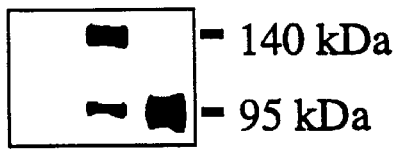
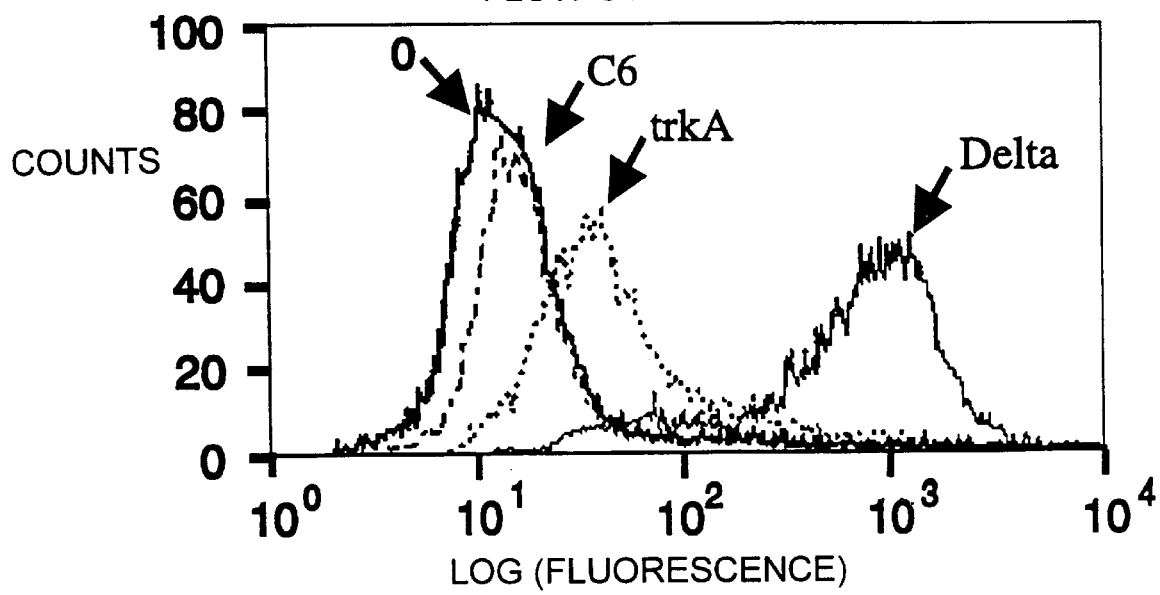

CANCER TREATMENT BY EXPRESSION OF DIFFERENTIATION FACTOR RECEPTOR

This application is a continuation-in-part of allowed patent application Ser. No. 08/310,287 entitled "CANCER TREATMENT BY EXPRESSION OF DIFFERENTIATION FACTOR RECEPTOR," filed Sep. 21, 1994, now U.S. Pat. No. 5,789,187; and this application claims priority to provisional patent application Serial No. 60/014,466, filed Mar. 21, 1996.

This invention was made with Government support under NIH grant no. R01 NS21716 awarded by the National Institutes of Health. Accordingly, the U.S. Government has certain rights in this invention.

The technical field of this invention is gene therapy of brain tumors. More particularly, this invention relates to inhibition of or reduction in tumorigenicity of cells within neural tumors by transferring a nucleic acid encoding a tyrosine kinase receptor for a differentiation-inducing factor into such cells and inducing expression of the nucleic acid.

BACKGROUND OF THE INVENTION

The nervous system is derived from multipotential precursor cells that maintain a closely regulated inverse relationship between cell proliferation and differentiation, as demonstrated in FIG. 1, which employs tissue culture of a neural tumor cell line. In the central nervous system, these precursor cells commit to a specific differentiation pathway shortly after their last mitosis. In the peripheral nervous system, sensory neurons differentiate following withdrawal from the cell cycle, but sympathetic neuroblasts begin to differentiate while still mitotically active. The molecular basis of the coupling between neuronal differentiation and cell proliferation is a problem of current interest which has been extensively studied using cell lines derived from neural tumors. The coupling between neuronal differentiation and cell proliferation is highly relevant to the etiology of neural tumors, in which the regulation of these two cell processes is disrupted.

Neuronal differentiation is induced and maintained by proteinaceous growth factors known as the neurotropins. Several neurotropins are known at this time: nerve growth factor (NGF), brain derived growth factor (BDNF) and neurotrophin-3 (NT-3). Neurotrophins mediate differentiation by binding to and activating high-affinity ($K_d \approx 10^{-11}$ M) receptor tyrosine kinases called Trk receptors which appear to transduce most of their biological actions (Chao (1992) *Neuron* 9:583–93; Hosang et al. (1985) *J. Biol. Chem.* 260:655–62; Schecter et al. (1981) *Cell* 24:867–74; and Sutter et al. (1979) *J. Biol. Chem.* 254:5972–82; Kaplan et al. (1991) *Science* 252:554–558; Klein et al. (1991) *Cell* 65:189–197). Activated TrkA is critical for initiating NGF signal transduction, while BDNF binds to a closely related TrkB receptor and NT-3 binds to the TrkC receptor.

Transmembrane receptor tyrosine kinases (RTKs) such as the Trk receptors generally function as molecular switches for transduction of signals from a cell's extracellular milieu, across the cell membrane, into the cytoplasm, and ultimately into the nucleus. Extracellular binding of a cognate ligand to its RTK results in receptor dimerization and autophosphorylation, followed by tyrosine phosphorylation of a specific subset of cellular protein substrates. Ultimately DNA synthesis and cell proliferation or differentiation results from signal transduction via an RTK. A large number of RTKs are known, for example, the epidermal growth factor receptor (EGFR), the platelet derived growth factor receptor (PDGFR), the macrophage colony stimulating factor receptor (CSF-1R), the various fibroblast growth factor receptors (FGFR), the insulin receptor, and the like. The EGFR and PDGFR are known to be involved in glioma growth and progression (see, e.g., Agosti et al. (1992) *Virchows Archiv. A. Pathol. Anat.* 420:321–5; Torp et al. (1991) *Cancer Immunol. Immunother.* 33:61–4; Fleming et al. (1992) *Cancer Res.* 52:4550–3. Additionally both EGF and PDGF tend to promote motility in in vitro assays (compared to NGF which tends to inhibit motility) (Chicoine et al. (1995) *Neurosurg.* 36:1165–71). Chimeric receptors of EGF and PDGF extracellular domains with the TrkA intracellular domain have been reported (Obermeier et al. (1993) *EMBO J* 12:933–41) and shown to autophosphorylate and initiate signal transduction in response to EGF and PDGF, respectively.

Recent clinical studies suggest that the TrkA receptor plays a critical role in neuroblastoma, one of the most common pediatric solid tumors. Patients whose tumors express significant levels of TrkA have a good chance for survival, while patients whose tumors lack TrkA respond poorly to therapy (Kogner et al. (1993) *Cancer Res.* 53:2044–2050; Nakagawara et al. (1993) *New Engl. J. Med.* 328:847–854; Suzuki et al. (1993) *J. Natl. Cancer Inst.* 85:377–384). Neuroblastoma frequently occurs during infancy, with the primary lesion in the adrenals and sympathetic chain and metastases to lymph nodes, liver, skin, and bone marrow. This tumor is difficult to treat as common modes of chemotherapy have harsh side effects on normal infant tissue. A variety of modalities have been used to treat neuroblastoma, such as surgery, radiotherapy, and chemotherapy, with varying degrees of success. For many patients, neuroblastoma continues to be fatal.

Cells within neuroblastoma tumors resemble those found in normally developing tissue of the sympathetic nervous system. Neuroblastomas may contain undifferentiated, closely packed spheroidal cells that closely resemble migrating neural crest cells of early embryos (neuroblasts), along with more differentiated cells whose immature nerve fibers tangle, thereby forming a rosette which is the first recognizable sign of neuronal differentiation. Some neuroblastomas undergo spontaneous regression or maturation to benign ganglioneuromas. The similarity of neuroblastoma cells to neuroblasts and the ability of neuroblastoma cells to spontaneously mature to a more benign form indicate that the disease may originate as the result of a block of differentiation of a sympathetic precursor cell.

Another neural tumor, glioma, is a family of cancers comprising the most common adult-onset neurological neoplasms such as malignant astrocytoma (or glioblastoma or malignant glioma), oligodendroglioma, and ependymoma, along with the juvenile onset neoplasms such as juvenile pilocystic astrocytoma (JPA) and the uncommon gangliogliomas. Expression of functional Trk receptors has not been reported for gliomas (Oelmann et al. (1995) *Cancer Res.* 55:2212–9), though neurotrophin production occurs with fairly high frequency. NGF is secreted by many glioma cell lines (Arnason et al. (1974) *J. Clin. Invest.* 53:2a; Longo et al. (1974) *Proc. Natl. Acad. Sci. USA* 71:2347–9; and Reynolds et al. (1981) *J. Neurosci. Res.* 6:319–25).

While most gliomas are difficult to treat and are ultimately untreatable, there are a few uncommon forms of glioma which are neither aggressive nor invasive. In fact, some patients with these rare gliomas can be followed without treatment for years; others can be effectively treated and even cured with surgery alone. Two types of glioma that behave in such a benign fashion are the uncommon gangliogliomas and JPA. The former tumor, composed of both neoplastic astrocytes and neurons, tends to occur in the temporal lobe of children and behaves very indolently. JPA, characteristically identified histologically by the presence of Rosenthal fibers and microcystic changes, can present as a large cystic mass that often produces symptoms by compressing neighboring structures and causing hydrocephalus. Nevertheless, they are curable by surgery alone, even when they attain significant size. JPA appears to be incapable of invading surrounding tissues.

In contrast, malignant glioma cells produce very invasive brain tumors with infiltration of both white and grey matter (Bjerkvig et al. (1986) *Cancer Res.* 46:4071–912). At the time of diagnosis, microscopic extension through much of the neural axis by malignant glioma is the rule (Burger et al. (1980) *Cancer* 46:1179–86; Kelly et al. (1987) *J. Neurosurg.* 66:865–74; Moser (1988) *Cancer* 62:381–90; and Salazar et al. (1976) *Int. J. Radiat. Oncol. Biol. Phys.* 1:627–37). Extension by motile invading cells underlies the incurability by surgery of most gliomas, even when they appear small and restricted in nature. Because gliomas are believed to arise from transformed astrocytes or their immediate precursors, glioma differentiation therapy has been primarily directed at increasing astrocytic differentiation, despite the observation that increasing glial fibrillary acidic protein (GFAP), a specific astrocytic marker, does not correlate with prognosis of these tumors (Delpech et al. (1978) *Br. J. Cancer* 37:33–40; Eng et al. (1978) *J. Histochem. Cytochem.* 26:513–23; and Chambers et al. (1991) *J. Veuro-Oncol.* 11:43–8). In fact, no significant therapeutic advances have been made in treatment of malignant gliomas since the landmark BTCG studies over 15 years ago demonstrated a survival advantage for patients with malignant gliomas who received radiation and single agent chemotherapy (Walker et al. (1978) *J. Neurosurg.* 49:333–43; and Walker et al. (1980) *NEJM* 303:1323–9). Cutting edge molecular technologies have led to a better understanding of glioma biology but have not as yet yielded clinical dividends. The median survival for patients with glioblastoma multiforme remains in the range of one year.

Glioma cells for the most part resemble normal glia and are frequently used by neurobiologists as paradigms for glial cells. Glioma tumor progression can be envisioned as an adaptation to local environmental changes or regulatory imbalances. In order for glioma cells to invade normal brain, they must escape from the parent tumor into the surrounding extracellular matrix, hydrolyze matrix components, and migrate through the matrix (Chicoine et al. (1 995) *J. Neurosurg.* 83:665–71). Glioma invasion into normal brain tissue thus represents the culmination of a series of events involving cell-cell interactions, tumor cell proteinases, adhesion molecules and chemoattractants.

A large number of cell lines have been developed from neuroblastomas (see, e.g., Chen, et al. (1990) *Cell Growth and Differentiation* 1: 79–85). For example, the SH-SY5Y line was developed from a bone marrow biopsy of a neuroblastoma patient whose primary thoracic tumor had metastasized (Biedler, et al. (1978) *Cancer Res.* 38, 3751–3757). The LAN5 cell line was similarly developed from a primary tumor (Seeger, et al. (1982),*J. Immunol.* 128: 983–989). The HTLA230 cell line, isolated from a patient with Stage IV neuroblastoma, has been employed to demonstrate the response of TrkA-expressing neuroblastoma cells to nerve growth factor, both in vitro and in vivo (Matsushima et al. (1993) *Mol. Cell. Biol.* 13, 7447–7456).

A number of different glioma cell lines have been used to study tumorigenicity, for example, human U-87 and U-373, and rat RT-9 and C6. The C6 rat glioma cell line is well characterized (McKeever et al. (1987) *Am. J. Pathol.* 127:358–72; and Peterson et al. (1994) *J. Neurosurg.* 80:865–75), grows well in vivo in non-immunosuppressed rats, and has been recognized as an experimental model of human glioblastoma multiforme (GBM) (Kaye et al. (1986) *Cancer Res.* 46:1367–73). After implantation, C6 cells also rapidly and extensively invade rat central nervous system (Chicoine et al. supra. Bernstein et al. (1990) *Neurosurg.* 26:622–8; and Bernstein et al. (1991) *Neurosurg.* 28:652–8), and movement of homografted C6 cells in brain suggests these cells actively migrate as individual cells in addition to invading as a mass (Bernstein et al. (1991) *Neurosurg.* 28:652–8). The capacity of C6 cells to aggressively invade both en masse and as single cells is very reminiscent of the clinical situation. Recently, C6 cells which do not express Trk receptors nor respond to NGF were transfected with a trkA-encoding vector (Colangelo et al. (1994) *Glia* 12:117–27). Exposure of transfected cells to NGF resulted in increased induction of tyrosine phosphorylation of $gp140^{trk}$, induction of c-fos mRNA and morphologic changes and (weakly) induction of cell growth.

De Ridder (*Neurosurg.* (1992) 31:1043–8) demonstrated that in vitro invasiveness of cells derived from primary brain tumor explants correlates with clinical malignant behavior. Additionally, a variety of agents have been shown to stimulate in vitro motile responses including host-derived scatter factors (Ohnishi et al. (1993) *Biochem. Biophys. Res. Commun.* 193:518–25), growth factors, components of the extracellular matrix and tumor secreted factors (Lund-Johansen et al. (1990) *Cancer Res.* 50:6039–44; and Chicoine et al. (1995) *Neurosurg.* 36:1165–71).

The side effects of known brain cancer therapy methods necessitate development of "natural" but highly-specific pharmaceutical treatments, such as various substances that promote differentiation of proliferating neuroblastic cells. At this time, however, none of the candidates for such natural therapeutic approaches have proven successful. Accordingly, methods are needed for inducing malignant brain tumors to become less motile, less proliferative, less invasive, and hence less malignant, or for inducing cells within such tumors to become less tumorigenic, for example, by differentiating into their non-malignant counterparts.

SUMMARY OF THE INVENTION

The present inventors have discovered that when a nucleic acid encoding a RTK comprising a cytoplasmic domain of a neurotrophin RTK is incorporated into a neoplastic neural cell, the motility, ability to proliferate, and tumorigenicity of the cell are reduced, while its morphology remains basically unaffected. In some neural tumor cells, the presence of the neurotrophin RTK cytoplasmic domain induces apoptosis. Surprisingly, the reductions in motility, ability to proliferate, and/or tumorigenicity observed in such RTK-expressing tumor cells occurs in the absence of added cognate differentiation factor of the receptor. These findings have been exploited to develop the present invention, which includes methods of treating a neurological tumor cell in vitro and in vivo, and of inhibiting or reducing its motility, ability to proliferate and/or tumorigenicity in vitro and in vivo.

The methods of the invention are generally directed to induction of benign tumor behavior. The present inventors have demonstrated that growth and invasiveness of a neural tumor may be reduced in vivo by incorporating a RTK comprising a cytoplasmic domain of a neurotrophin RTK into the cells of the tumor and effecting expression of the receptor. Thus in accordance with the present invention, a neural tumor may be rendered less tumorigenic through expression of a neurotrophin RTK cytoplasmic domain in the tumor.

In one embodiment, the invention provides a method of treating a neurological tumor in a mammal comprising the steps of: providing a vector comprising a first nucleic acid encoding an intracellular domain of a tyrosine kinase receptor for a neurotrophin; and administering to the mammal a therapeutically effective amount of a pharmaceutical composition comprising the vector and a physiologically acceptable carrier, wherein the nucleic acid encoding the receptor is expressed in the tumor.

BRIEF DESCRIPTION OF THE DRAWINGS

The foregoing and other objects of the present invention, the various features thereof, as well as the invention itself may be more fully understood from the following description, when read together with the accompanying drawings.

FIG. 5A is a photographic representation of the results of RT-PCR on an agarose gel demonstrating the presence of the trkA or trkAΔ DNA in transfected C6 cells.

FIG. 5B is a representation of a Western blot demonstrating the expression of the TrkA or TrkAΔ receptor in transfected C6 cells, where 0=control monoclonal antibody (IgG$_3$).

FIG. 5C are fluorescent cytograms demonstrating anti-TrkA monoclonal antibody binding to C6, C6$^{trkA}$, and C6$^{trkA}$ cells.

DETAILED DESCRIPTION OF THE PREFERRED EMBODIMENTS

Figure 1:
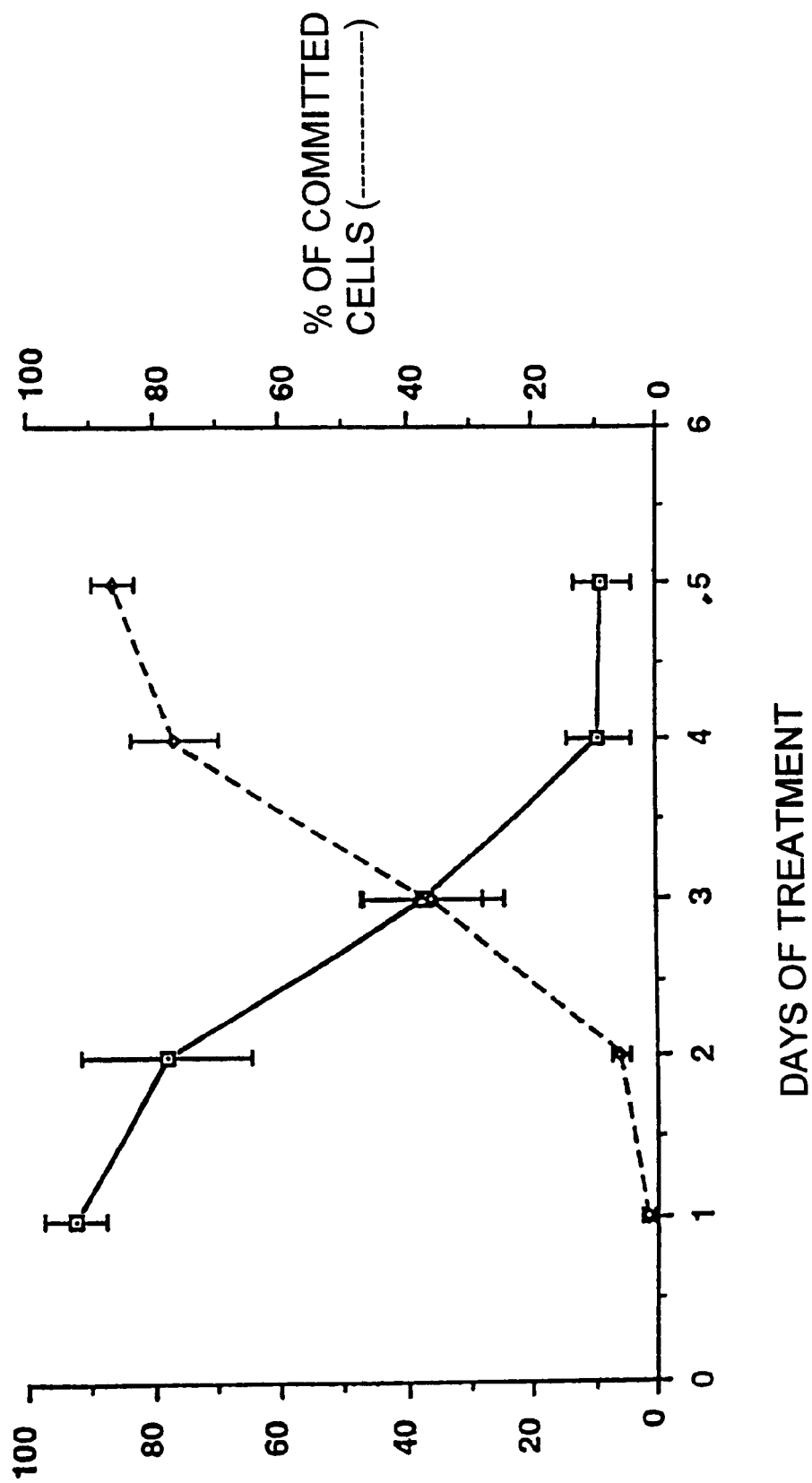
FIG. 1 is a graphic representation of the relation between commitment to differentiation and irreversible cessation of proliferation, in which SH-SY5Y cells were treated with nerve growth factor and aphidicolin for one to five days and then treated with nerve growth factor for six days. Proliferation was measured by BrdU labeling. Differentiation was measured by microscopic inspection and scoring for neurite extension at five days.

The patent and scientific literature referred to herein establishes the knowledge that is available to those with skill in the art. The issued U.S. patents, allowed applications, and other publications cited herein are hereby incorporated by reference.

This invention provides a method of treating neural tumor cells which results in a reduction in the cells' ability to proliferate in a semi-soft medium, thus resulting in a reduction of the tumorigenicity of the cells. The method of the invention also reduces the neural tumor cells' tumorigenicity in vivo, by reducing their ability to proliferate, to migrate, and/or by increasing their rate of apoptosis. As used herein, the term "tumorigenicity" is meant to encompass the ability of a cell to form a tumor, as measured in vitro by the ability of the cell to form a colony in a semi-solid medium, by the proliferative rate of the cell, by the motility of the cell, or as measured by actual tumor formation in an in vivo experimental model. The term "motility" encompasses both invasiveness, or migration of a tumor cell within an organ, and metastasis, or migration a cell to a different organ.

In the method of the invention, a vector is provided which comprises a nucleic acid encoding an RTK that mediates cellular proliferation or differentiation through the action of an intracellular signaling domain derived from a neurotrophin RTK. As used herein, the term "vector" is meant to encompass a structure composed of covalently linked nucleotides which is able to enter a cell with the receptor-encoding nucleotide sequence. In preferred embodiments, the vector is an expression vector, plasmid, retrovirus, adenovirus, adeno-associated virus, Herpesvirus, or other transfer vehicle known in the art which integrates into the cell genome once inside. Alternatively, the nucleotide sequence may be a part of an episome or attached to a particle (used in particle bombardment) which remains separate from the cell genome and is capable of independent replication and expression. Preparation of such vectors and the integration of the nucleotide sequence encoding the receptor are well known in the art (see, e.g., Sambrook et al. (1989) *Molecular Cloning, A Laboratory Manual*, Cold Spring Harbor Laboratory Press, pp. 3.2–3.58; Kriegler (1990) *Gene Transfer and Expression*, Stockton Press, WY; Wolff (ed.) *Gene Therapeutics*, Birkhauser Press, Boston, Mass., 1994); see also, Example 2.

The RTK expressed in the method of the invention comprises an intracellular domain capable of mediating phosphorylation of a specific tyrosine residue on cognate intracellular proteins which in turn are capable of mediating proliferation or differentiation of neural cells. A "differentiated cell" as defined herein may have an altered morphology associated with one lineage or differentiated state, and may express nucleic acids associated with one particular lineage or differentiated state. For example, when small, round neuroblastoma or glioma cells differentiate, they become extended and develop neurite outgrowths. The RTK expressed in the method of the invention comprises a cytoplasmic (i.e., intracellular) domain of a neurotrophin RTK such as TrkA, TrkB, or TrkC, and the like. The cytoplasmic tyrosine phosphorylating domain expressed in the method of the invention may be contained within a homologous neurotrophin RTK, i.e., one having all of its domains derived from a single RTK, or the domain may be derived from a chimeric receptor e.g., the extracellular domain is derived from one RTK and the intracellular and/or transmembrane domain is derived from a second RTK. Nucleic acids encoding chimeric RTKs for use in the method of the invention may be prepared by operatively attaching a nucleic acid encoding an extracellular domain from any RTK to a nucleic acid encoding the intracellular domain of a neurotrophin RTK. As used herein, "operatively attached" means that the nucleic acids encoding the intracellular and extracellular domains of the RTKs are combined on or incorporated into a vector in an orientation which, when the combined nucleic acid is expressed, produces an active RTK. Methods for operatively attaching nucleic acids to each other using recombinant technology are known, as described above and in Example 2. In chimeric receptor embodiments, the extracellular portion of the RTK comprises a domain which recognizes and specifically binds to a cognate differentiation factor such as nerve growth factor (NGF), an interleukin, a fibroblast growth factor, neurotrophin-3, neurotrophin-4, insulin, insulin-like growth factor, brain derived neurotrophic factor, epidermal growth factor, platelet-derived growth factor, macrophage colony stimulating factor, and the like. The nucleic acid may optionally comprise nucleic acids encoding other RTK domains such as a transmembrane domain and the like, which may be derived from any RTK. Preferred embodiments of chimeric RTKs expressed in the method of the invention comprise an EGF receptor or a PDGF receptor extracellular domain, in combination with a TrkA intracellular domain, as described in Example 2.

In accordance with the method of the invention, the vector containing a nucleic acid encoding the neurotrophin RTK cytoplasmic domain is transferred to the tumor cell in such a way that the nucleic acid is expressed in the tumor cell and thereby the RTK protein is present in the cell membrane. Any method may be used to transfer the vector to the tumor cell. When the vector is transferred into the tumor cell in vitro, transfer may be accomplished by electroporation, transfection, transformation, particle bombardment, and the like. Electroporation involves the application of brief, high-voltage electric pulses to the cells, leading to the formation of nanometer-sized pores in the plasma membranes. DNA is taken directly into the cell cytoplasm either through these pores or as a consequence of redistribution of membrane components that accompanies closure of the pores (see, e.g., Sambrook et al., supra, pp. 16.54–55). Any transfection method may be used to transfer the vector into the tumor cell. For example, calcium phosphate- or DEAE-dextran-mediated transfection enables a nucleic acid to enter a cell by endocytosis. The nucleic acid is then transferred to the nucleus where it can be expressed by the protein synthetic machinery of the cell (see, e.g., Sambrook et al., supra, pp. 16.33–16.46). In addition, the polycation polybrene allows the introduction of low molecular weight DNAs into cell lines that are relatively resistant to transfection by other methods (see, e.g., Sambrook et al., supra, p. 16.47). Particle bombardment refers to a method wherein small particles are coated with DNA and then propelled at high speed into the cell. In some embodiments, the nucleic acid is incorporated into the genome of the cell. In other embodiments, the nucleic acid remains separate from the cell genome, within the vector which is an independent episome, or attached to the particle following particle bombardment. Another mode of transferring a nucleic acid into a cell is protoplast fusion. In this method, protoplasts derived from bacteria carrying high numbers of copies of a plasmid of interest are mixed directly with cultured mammalian cells. After fusion of the cell membranes, usually with polyethylene glycol, the contents of the bacteria are delivered into the cytoplasm of the cells and the plasmid is transferred to the nucleus (see, e.g., Sambrook et al., supra, p. 16.48–53).

When the vector is transferred into the tumor cell in vivo, transfer may be accomplished via intravenous or intratumoral injection, with or without additional treatments to enhance the permeability of the blood-brain barrier. Alternatively, the vector comprising the RTK-encoding nucleic acid may be administered to cell ex vivo, and the cell containing the vector transferred into the tumor in vivo.

Transfer of the vector into the tumor cell may be monitored in vitro by observing proliferation of the cell or (for in vivo embodiments) of a representative aliquot of vector-containing cells in semi-solid medium. As used herein, "semi-solid medium" refers to a medium which is not liquid or solid, such as soft agar, soft agarose, or soft methylcellulose. Reduction in tumor cell proliferation or motility in tissue culture corresponds to a reduction in tumorigenicity. Cell proliferation may be monitored in accordance with the invention using any method, for example, by counting the number of tumor cells present, or by determining DNA or cellular protein content of tumor cells. Alternatively, cell apoptosis may be observed in monitoring the progress of the method of the invention.

Cell proliferation may be monitored in vivo, for example, by measuring tumor size, and cell motility may be monitored in vivo by screening for metastasis or invasiveness of the tumor in the mammal. Proliferation and metastasis of tumor cells may also be monitored in vivo using labeled imaging agents and imaging methods such as radiography, PET, SPECT, and the like, or using non-invasive scanning methods such as NMR, CAT, and the like. Reductions in tumorigenicity of tumor cells treated by the method of the invention may be monitored using any of these techniques, alone or in combination.

Any type of neurological tumor cell may be treated using the method of the invention. For example, tumor cells present in a neurological tumor in a mammal, cells grown in culture, and cells derived from explants of in vivo tumors may be treated using the method of the invention. In some embodiments, such cells include neuroblastoma, glioma, lymphoma, carcinoma, leukemic, astrocytoma, and glioblastoma cells.

The RTK-encoding vectors are used in the method of the invention to treat neural neoplasms, such as neuroblastoma, astrocytoma, glioblastoma, and glioma in mammals, including humans. The method of the invention employs a therapeutic composition comprising the vector described above and a physiologically or pharmacologically acceptable carrier. As used herein, a "physiologically or pharmacologically acceptable carrier" includes any and all solvents, dispersion media, coatings, antibacterial and antifungal agents, isotonic and absorption delaying agents and the like which will not inactivate the ability of the vector to express itself in the neuroblastoma cell or to integrate into its genome into that of the cell. The use of such media and agents for pharmaceutically active substances is well known in the art. Except insofar as any conventional medium or agent is incompatible with the vector, its use in the therapeutic compositions is contemplated. Supplementary active ingredients can also be incorporated into the compositions.

In the method of the invention, the pharmaceutical composition is administered once or repeatedly to the tumor or site of neoplasm in a therapeutically effective amount. As used herein, the term "therapeutically effective amount" means the total amount of each active component of the pharmaceutical formulation or method that is sufficient to show a meaningful subject or patient benefit, i.e., a reduction in tumor size, arrest, or inhibition of tumor growth and/or motility or metastasis, and/or an increase in apoptosis, and/or a reduction the symptoms related to the presence of the tumor (e.g., lethargy, subconjunctival hemorrhages, gait impairment). When applied to an individual active ingredient (i.e., the vector), administered alone, the term refers to that ingredient alone. When applied to a combination, the term refers to combined amounts of the active ingredients that result in the therapeutic effect, whether administered in combination, serially or simultaneously. A "therapeutically effective manner" refers to a route, duration, and frequency of administration of the pharmaceutical formulation which ultimately results in meaningful patient benefit, as described above.

The therapeutically effective amount of the RTK-encoding nucleic acid or vector containing such nucleic acid in the pharmaceutical composition used in the method of the present invention will depend upon the nature and severity of the condition being treated, and on the nature of prior treatments which the patient has undergone. Preferably, the amount of nucleic acid encoding the RTK is from about 0.001 ng to about 100 mg per kg body weight. Initially, the attending physician will administer low doses of the composition and observe the patient's response. Larger doses of composition may be administered until the optimal therapeutic effect is obtained for the patient, and at that point the dosage is not increased further. It may. be desirable to administer simultaneously or sequentially a therapeutically effective amount of one or more of the therapeutic compositions of the invention to one individual as a single treatment episode. Ultimately, the attending physician will decide the amount of therapeutic composition with which to treat each individual patient.

Administration of pharmaceutical compositions to practice the method of the present invention can be carried out in a variety of conventional ways, such as by transdermal administration, intravenous injection, injection directly into or in the vicinity of the tumor, or by any other route of administration known in the art for administrating therapeutic agents, and may be followed by intermittent regimens. Administration of the pharmaceutical compositions in accordance with the invention may include treatment motalities which enhance the permeability of the blood/brain barrier.

When a therapeutically effective amount of the pharmaceutical composition used in the method of the invention is administered by injection, the pharmaceutical composition will preferably be in the form of a pyrogen-free, parenterally-acceptable, aqueous solution. The preparation of such parenterally-acceptable solutions, having due regard to pH, isotonicity, stability, and the like, is within the level of ordinary skill in the art of pharmacology. A preferred pharmaceutical composition for injection should contain, in addition to the vector, an isotonic vehicle such as Sodium Chloride Injection, Ringer's Injection, Dextrose Injection, Dextrose and Sodium Chloride Injection, Lactated Ringer's Injection, phosphate buffered saline (PBS), or other vehicle as known in the art. The pharmaceutical composition used in the method of the present invention may also contain stabilizers, preservatives, buffers, antioxidants, or other additives known to those of skill in the art. The pharmaceutical composition may also contain agents for enhancing the permeability of the blood/brain barrier and agents for enhancing cellular uptake of nucleic acids such as cyclodextrins cationic lipids, and the like.

The pharmaceutical formulation can be administered in bolus, continuous, or intermittent dosages, or in a combination of continuous and intermittent dosages, as determined by the physician and the degree and/or stage of illness of the patient. The duration of therapy with the pharmaceutical composition used in the method of the present invention will vary, depending on the unique characteristics of the RTK-encoding vector and the particular therapeutic effect to be achieved, the limitations inherent in the art of preparing such a therapeutic formulation for the treatment of humans, the severity of the disease being treated and the condition and potential idiosyncratic response of each individual patient. Ultimately the attending physician will decide on the appropriate duration of intravenous therapy with the pharmaceutical composition used in the method of the present invention, as, for example, described in Goodman and Gilman's *The Pharmacological Basis of Therapeutics* (8th Ed.) McGraw-Hill, Inc., New York (1993) pp. 62–83.

Figure 2:
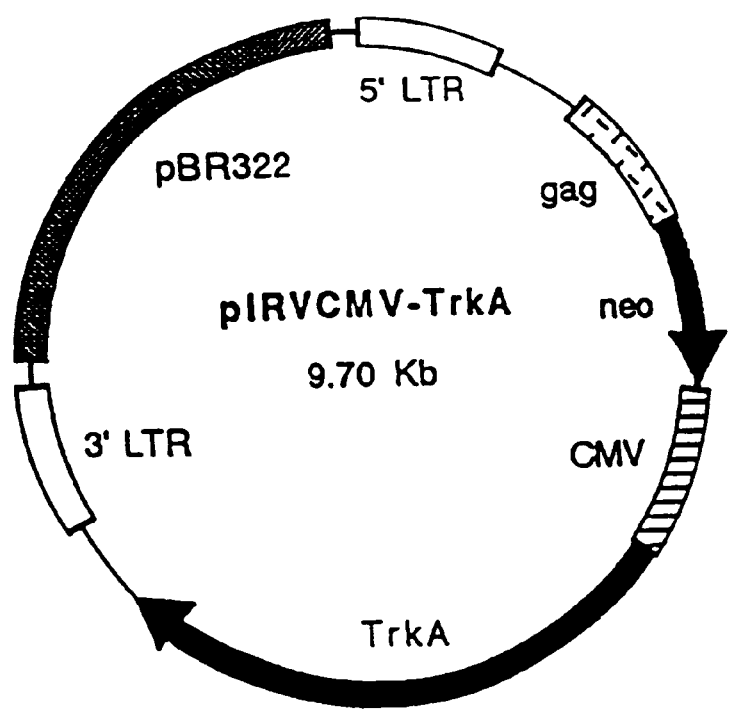
FIG. 2 is a map of the pIRVCMV-TrkA vector.
Figure 3:
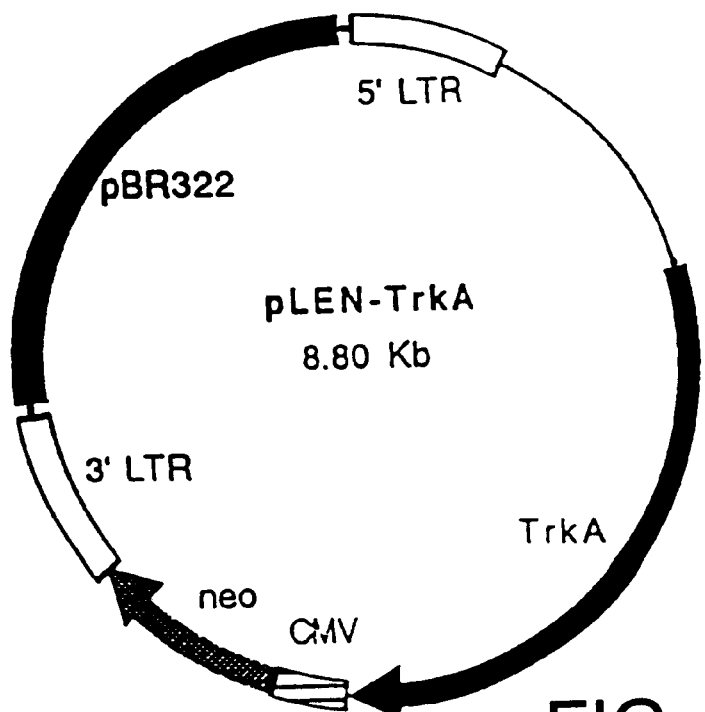
FIG. 3 is a map of the pLEN-TrkA vector.
Figure 4:
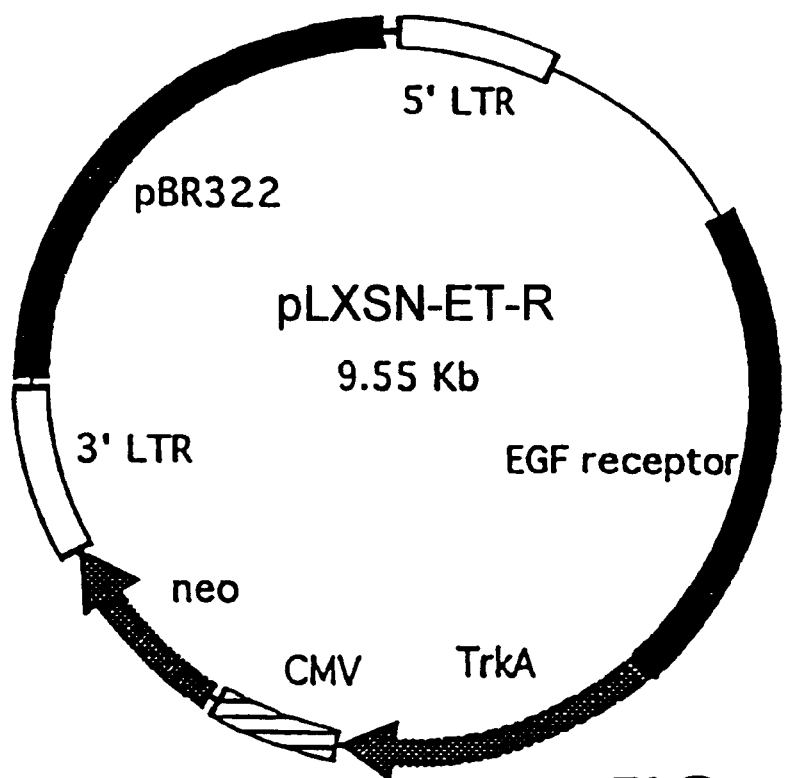
FIG. 4 is a map of the pLXSN vector which encodes a chimeric receptor including parts of both EGF receptor and TrkA.

Using recognized experimental models, the present inventors have shown that transfer of an intracellular domain of a neurotrophin RTK to a neural tumor cell decreases the cell's tumorigenicity. More particularly, copending allowed application Ser. No. 08/310,287, now U.S. Pat. No. 5,789,187, discloses methods of reducing a neural cell's ability to proliferate by transferring a vector encoding a RTK into the cell and culturing the cell in the absence of the RTK's ligand. The methods of application Ser. No. 08/310,287, now U.S. Pat. No. 5,789,187, were developed using the human neuroblastoma cell lines SH-SY5Y and LAN5 transfected with vectors including cDNAs encoding the entire human TrkA receptor. The vectors used for these studies are depicted in FIGS. 2 and 3, and the details of their construction are set forth in Example 2. In application Ser. No. 08/310,287, now U.S. Pat. No. 5,789,187, the method of the invention was shown to reduce tumorigenicity of neuroblastoma cells. The apparent mechanism of the reduced tumorigenicity of neuroblastoma cells demonstrated in application Ser. No. 08/310,287, now U.S. Pat. No. 5,789,187, was induction of differentiation, since neurite outgrowth was observed in cells treated in accordance with the invention.

The studies of application Ser. No. 08/310,287, now U.S. Pat. No. 5,789,187, were extended using the pLEN-TrkA vector of FIG. 3 transferred into C6 rat glioma cells. Endogenous TrkA protein expression has not been reported in human or in rat glioma cells. When grown in serum supplemented medium, the untransfected C6 cell line expressed no trkA MRNA or TrkA protein, nor was it responsive to NGF. Upon treatment with aphidicolin as described in Example 7, thereby reversibly inhibiting DNA polymerases $\alpha$ and $\beta$ and blocking the cell cycle at G1-S, the untransfected C6 cells immunostained positive for TrkA, and histochemical analysis indicated that the cells began to differentiate. However, in spite of the presence of the TrkA antigen and apparent differentiation, NGF produced no discernable effect on untransfected C6 cell growth rate in aphidicolin. Within a few days of aphidicolin removal, cells resumed growing at a normal rate and started assuming a flat polygonal appearance. No evidence that cells had undergone apoptosis upon NGF withdrawal was evident. Thus, the effects of aphidicolin on these cells are were reversible and, although these cells express TrkA, their response to NGF appears to be limited to an increase of process length.

Figure 6A:
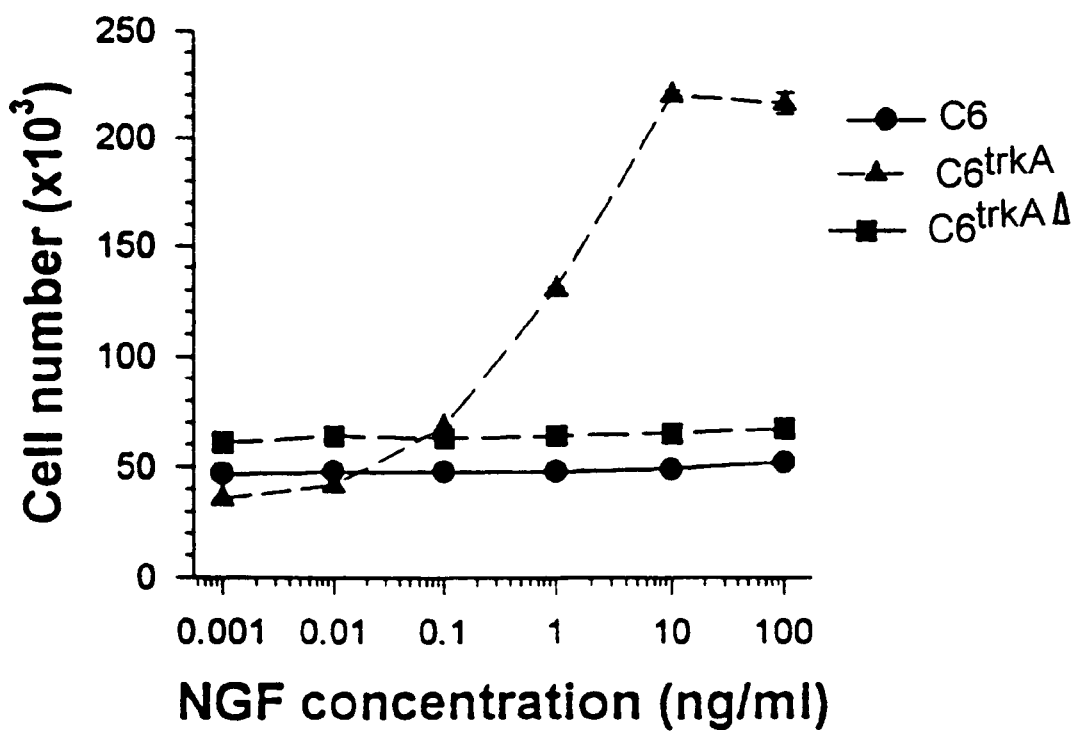
FIGS. 6A and 6B are two graphs representing the growth responsiveness of C6, C6$^{trkA}$, and C6$^{trkAΔ}$ cells to NGF.
Figure 6B:
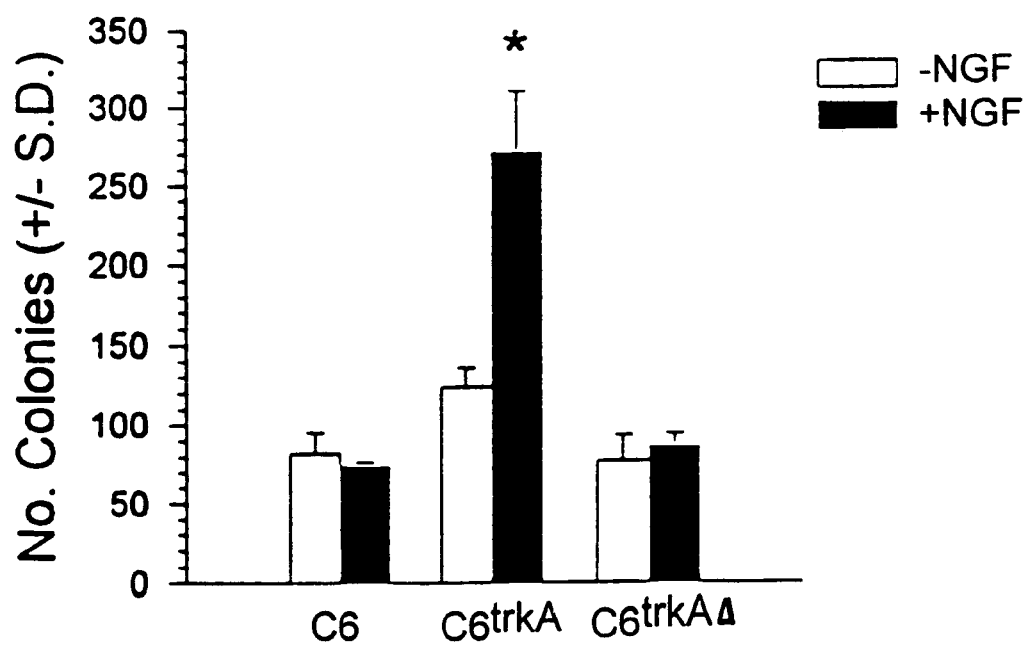

Using methodology described in Example 3, C6 cells were transfected either with the pLEN-TrkA vector that contained full length trkA (designated as $C6^{trkA}$) or with a derivative of pLEN-TrkA vector, pLEN-TrkA$\Delta$, that lacked an intracellular kinase domain (designated as $C6^{trkA\Delta}$). Both $C_6^{trkA}$ and $C6^{trkA\Delta}$ cells expressed mRNA encoding the extracellular TrkA domain, as assessed by RT-PCR (FIG. 5A) and bound a monoclonal antibody directed against the rat TrkA extracellular domain, as assessed by flow cytometry (FIG. 5C). Similarly, both transfectants stained immunohistochemically with monoclonal and polyclonal anti-TrkA antibodies. FIG. 5B is a Western blot showing that a 140 kD protein was expressed by $C6^{trkA}$ cells, corresponding to full length TrkA, and that a ~100 kD protein was expressed by $C6^{trkA\Delta}$ cells, corresponding to the truncated TrkA receptor. Transfection of the C6 cells with a full length TrkA receptor resulted in NGF responsiveness, as shown in FIG. 6, which was mediated by the TrkA intracellular domain, since transfection with the truncated trkA lacking a signal transducing domain resulted in no NGF responsiveness.

Figure 7:
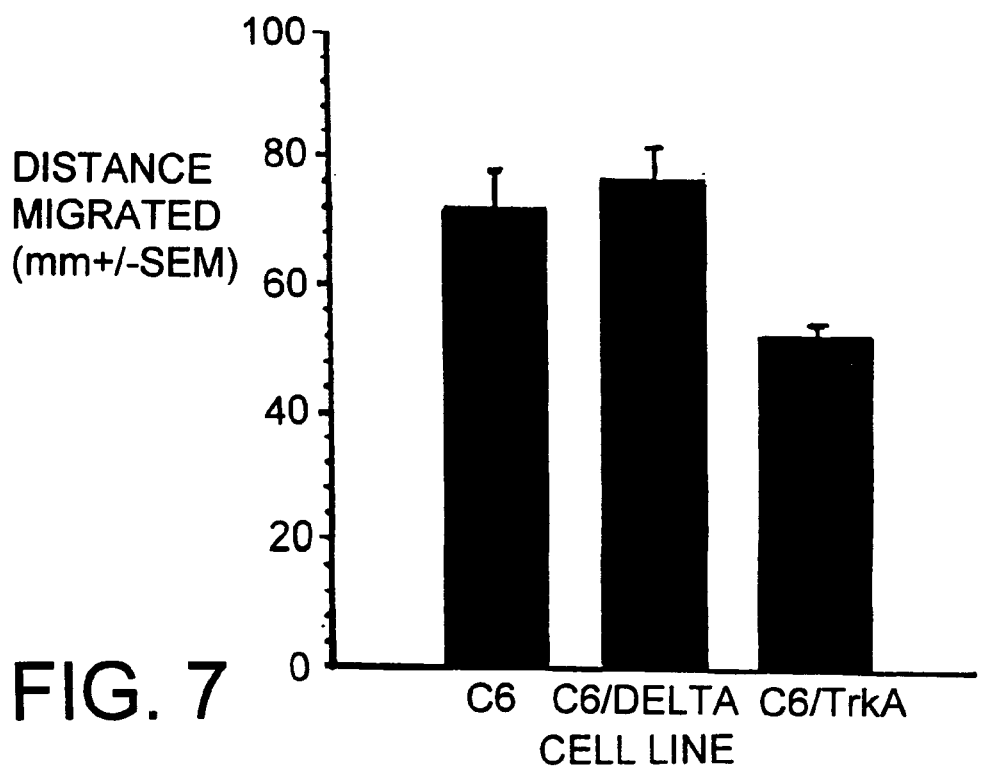
FIG. 7 is a bar graph depicting the ability of C6, C6$^{trkAΔ}$, and C6$^{trkA}$ cells to migrate in vitro.

As discussed above, in vitro invasiveness has been correlated with tumor malignancy, and in addition, more malignant tumors migrate more quickly (Chicoine et al. (1995) *Cancer* 75:2904–9). The in vitro scatter/motility assay of Example 11, is predictive of the reduction of a tumor cell's ability to migrate and of the induction of benignity in vivo. FIG. 7 shows that the method of the invention results in reduced tumor cell migration.

Figure 8:
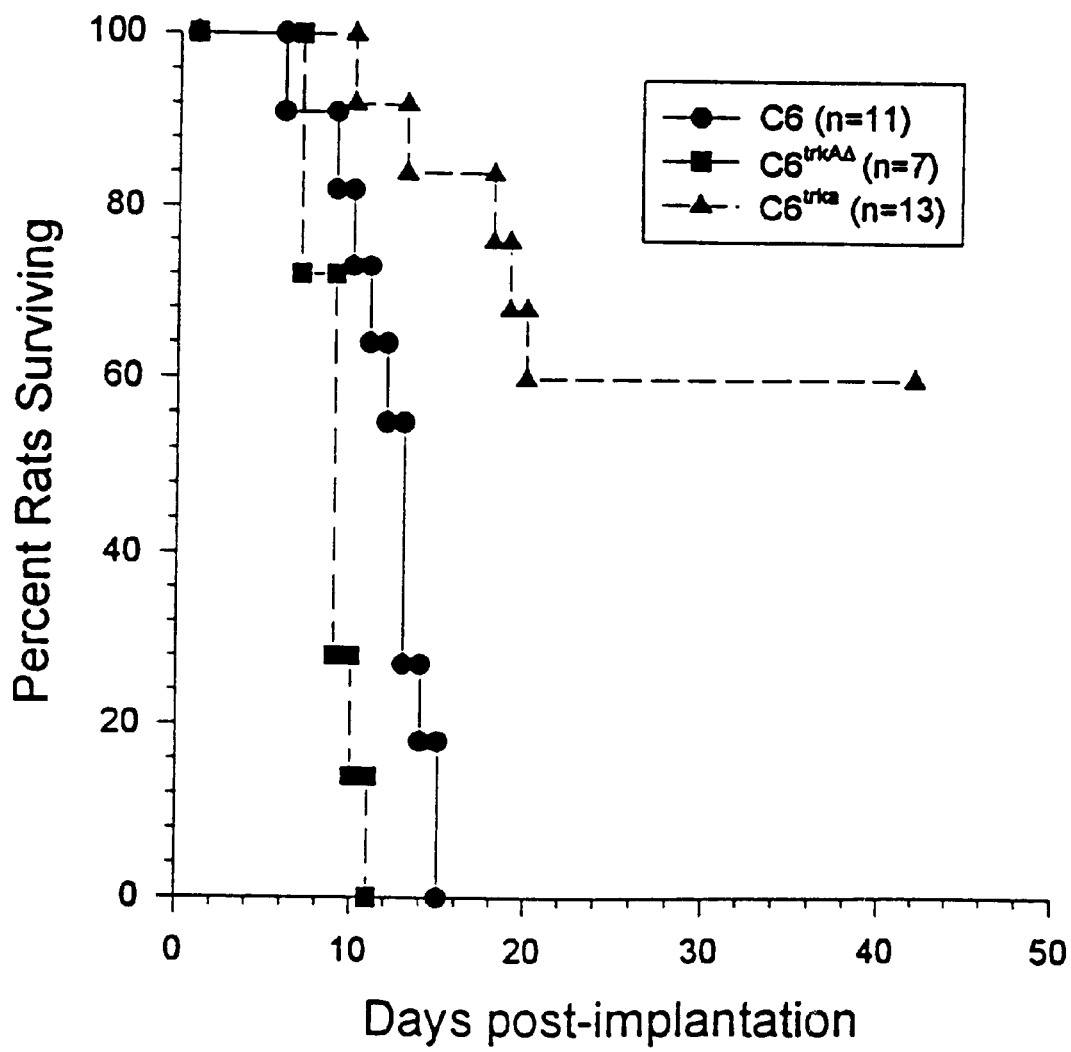
FIG. 8 is a graphic representation of the survival rates for rats inoculated with C6, C6$^{trkAΔ}$, or C6$^{trkA}$ cells.

Each of the transfected cell lines was implanted into rat brains as set forth in Example 12. The forebrains of 31 WKO rats were inoculated with $5 \times 10^6$ cells of either C6 (n=11), $C6^{trkA}$ (n=13), or $C6^{trkA\Delta\Delta}$ (n=7) cells and observed for up to 42 days. FIG. 8 depicts the survival rates for these differently treated rat groups. No rats harboring C6 or $C6^{trkA\Delta\Delta}$ cells survived fifteen days post-implantation, whereas 54% of rats inoculated with $C6^{trkA}$ cells were asymptomatic at the end of the 6 week experiment. A number of these long term survivors had appeared mildly ill between days 15–21. Usually, when rats implanted with C6 cells begin to show signs of such illness (i.e., subconjunctival hemorrhage, lethargy), they progress within a few days to death. The $C6^{trkA}$ rats, on the other hand, failed to demonstrate progressive signs and recovered completely to survive long term. By a log-rank test, rats harboring $C6^{trkA}$ thus survived significantly longer than either C6 ($P<0.001$) or $C6^{trkA\Delta\Delta}$ ($P<0.001$) animals.

The effect of TrkA expression on the ability of C6 cells to spread through host brain both as individual cells and as a rapidly expanding primary mass (Bernstein et al. (1990) *Neurosurg.* 26:622–628; and Goldberg et al. (1991) *Int. J. Dev. Neurosci.* 9:427–437) was examined. Five brains from rats injected with one of the three transfected cell lines were histologically examined. One rat each injected with C6 or $C6^{trkA\Delta\Delta}$ was sacrificed at day 11 post-implantation. Both rats were very ill at the time of sacrifice. Three $C6^{trkA}$ brains were examined: one asymptomatic rat was sacrificed at day 12 and another asymptomatic one was sacrificed at day 42. Another animal was symptomatic (i.e., with subconjunctival hemorrhage and lethargy) at time of sacrifice at day 27. The brains were processed and stained using hematoxylin and eosin staining, which revealed that all rats except for the one sacrificed at day 42 harbored macroscopic tumors. In all rats (including the $C6^{trkA}$ brains) in which macroscopic tumors were observed, the tumor mass itself at least superficially resembled glioblastoma multiforme (i.e., areas of necrosis and pseudopalisading). Both the C6 and $C6^{trkA\Delta\Delta}$ tumors encompassed a large portion of the brain, and numerous cells were detected infiltrating into normal surrounding brain. In contrast, the tumor found in the $C6^{trkA}$ animal sacrificed at day 12 was much smaller, although there was some hydrocephalus. The $C6^{trkA}$ rat sacrificed at day 27 had a larger mass which still appeared more circumscribed than in either of the other two lines at day 11.

One prominent feature which distinguishes the $C6^{trkA}$ tumors is the lack of invasion into the surrounding parenchyma, i.e., lack of tumor cell motility. In brain sections stained with hematoxylin and eosin, numerous infiltrating C6 and $C6^{trkA\Delta\Delta}$ tumor cells were detected in brain tissue. In contrast, the $C6^{trkA}$ tumors had a well defined margin with very few cells in the surrounding tissue. A similar pattern was observed when sections were immunostained for nestin, a primitive neuroepithelial marker, which is strongly positive in C6 glioma cells but is expressed at very low levels in normal adult brain. Thus trkA expression in accordance with the method of the invention suppresses tumor cell motility in vivo.

The proliferation potential of the tumors was assessed by staining brain sections for proliferation cell nuclear antigen (PCNA), a marker for cell proliferation. Tumors derived from C6 and $C6^{trkA\Delta\Delta}$ cells were 2–3 fold more positive for PCNA than control brain. Tumors formed by $C6^{trkA}$ or $C6^{trkA\Delta\Delta}$, but not C6, cells were TrkA-positive, as determined using the anti-TrkA monoclonal antibody TA-1 (Ross et al. (1996) *J. Cell Biol.* 132:945–953) which is specific for the TrkA extracellular domain. Thus, trkA expression in accordance with the method of the invention suppresses cell proliferation in vivo.

These tumors were also examined for differentiation markers. Although $C6^{trkA}$ tumors were distinguished by their retention of TrkA immunostaining, very little expression of GFAP and neurofilament were noted for C6, $C6^{trkA}$, and $C6^{trkA\Delta\Delta}$. With the lack of any phenotypically appearing neurons as well, therefore, induction of a neuronal phenotype (i.e., development of a ganglioglioma) does not appear to be the mechanism by which the method of the invention effects reduced tumorigenicity when applied to gliomas.

A statistical analysis of 48 high power fields per tumor type revealed a significant difference in the number of apoptotic cells visualized by TUNEL staining for apoptotic damage to DNA. Specifically, $C6^{trkA}$ tumors contained a greater number of apoptotic cells than either C6 or $C6^{trkA\Delta\Delta}$. Enhanced apoptosis may lead to slower growth or even regression of gliomas treated using the method of the invention.

Tumor growth was also assessed in nude mice in a visible location in which measurements can be made, using the methods set forth in Example 13. Male nude mice (n=3) were subcutaneously inoculated in their right flank with either $5 \times 10^6$ C6, $C6^{trkA}$, or $C6^{trkA\Delta\Delta}$ cells and followed every other day until visible tumors appeared, after which measurements of the two largest diameters were made every other day so that a tumor volume could be calculated. One week post-inoculation, all mice harboring C6 and $C6^{trkA\Delta\Delta}$ cells had visible tumors while none of the $C6^{trkA}$ animals had palpable masses. By two weeks post-inoculation, however, tumors appeared in all $C6^{trkA}$ mice, although they were still significantly smaller. Furthermore, their appearance differed from the tumors produced by the other two lines in that they appeared much less infiltrative into surrounding tissues. Over the ensuing weeks, however, the $C6^{trkA}$ tumors continued to grow and by day 25, all mice harbored large tumors on gross examination.

Using methods described in Example 3, C6 clones have been created which express full length human EGF and PDGF receptors as well as the chimeric ETR and PTR receptors containing the extracellular domains of the respective EGF and PDGF receptors ligated to the membrane and intracytoplasmic TrkA TK signaling domain. These four lines have been assessed for the effects of their respective ligands. Modest growth stimulatory effects were observed on all chimeric transfectants, through these effects were not as profound as those observed when NGF was applied to $C6^{trkA}$ cells. The effects of inoculating both $C6^{EGFR}$ and $C6^{PDGER}$ cells into rat brains have also been assessed and found to result in median survivals of 11 and 13 days (n=3 for each line).

Thus, using a variety of recognized experimental models, the present inventors have clearly demonstrated that transfer of an intracellular domain of a neurotrophin RTK to a tumor cell reduces the cell's tumorigenicity, both in vitro and in vivo. The method of the invention may act by any of a variety of mechanisms, and the precise mechanism of action appears to vary with tumor type. For example, when applied to gliomas, one possible mechanism of action for the method of the invention is induction of more benign tumor behavior through a decrease in invasive capacity. Another possible mechanism of action when the method is applied to gliomas is through induction of apoptosis. When the method of the invention is applied to neuroblastomas, tumor cell differentiation is induced. Other mechanisms of action may be applicable when the method of the invention is used to treat other neural tumors. Regardless of the mechanism of action, when a nucleic acid encoding an RTK comprising the intracellular domain of TrkA is introduced into a tumor cell in accordance with the method of the invention, the tumorigenicity of the tumor cell is reduced.

The following examples illustrate the preferred modes of making and practicing the present invention, but are not meant to limit the scope of the invention since alternative methods may be used to obtain similar results.

EXAMPLE 1

Cell Culture

SH-SY5Y cells were grown at 37° C. in RPMI 1640 medium (GIBCO BRL, Gaithersburg, Md.) supplemented with 10% fetal bovine serum (Sigma Chemicals, St. Louis, Mo.) and 100 µg/ml of gentamicin. For differentiation studies, cells were plated ($1.5 \times 10^5$ to $5 \times 10^5$ cells/dish) in 35-mm Primaria dishes (Falcon, Franklin Lakes, N.J.). One hundred ng/ml NGF (2.5 S; Bioproducts for Science, Indianapolis, Ind.) and/or 0.3 µM aphidicolin (Sigma Chemicals, St. Louis, Mo.) were added every 2–3 days. Cell proliferation was assessed by BrdU labeling, as described by LoPresti et al. (*Cell Growth Diff.* (1992) 3:627–635).

The LAN5 cell line differs from the SH-SY5Y line in that the N-myc protooncogene is amplified in LAN5 cells but not in SH-SY5Y. Hence, the etiology leading to the SH-SY5Y tumor differs from the LAN5 tumor. Cells were grown at 37° C. in RPMI 1640 medium (GIBCO BRL, Gaithersburg, Md.) supplemented with 10% fetal bovine serum and 100 µg/ml gentamicin.

C6 rat glioma cells were obtained from the American Type Culture Collection (ATCC CCL 107, (Rockville, Md.), and maintained in MEM at 37° C. and at 5% $CO_2$.

EXAMPLE 2

Preparation of Vectors

The pIRVCMV-TrkA vector was prepared using the pIRVCMV plasmid (Hempstead et al. (1992). *Neuron* 9:883–896). This plasmid includes an ampicillin resistance gene and origin of replication for growth in bacteria, a neomycin-resistance gene (neo) for selection in eukaryotic cells, a cytomegalovirus (CMV) promoter for expression of inserted nucleic acids, and long terminal repeats (LTR) for insertion into eucaryotic genomes (see FIG. 11). pIRVCMV was cleaved with BamHI and ClaI, and a cDNA including all of the coding sequence for TrkA was inserted downstream from the CMV promoter and ligated. The ligation mix was used to transform bacteria. A clone (pIRVCMV-TrkA) was selected and used for all further experiments. Prior to electroporation, pIRVCMV-TrkA was cleaved with NotI. This procedure is designed to increase production of the TrkA protein. During insertion of pIRVCMV-TrkA into the genome, the plasmid is linearized. By cleaving at the NotI site, the linearization occurs in a region not required for expression of the trkA sequence.

The plasmid pLEN-TrkA was prepared by cleaving the plasmid pLEN Obermeier, et al. (1994) *EMBO J.* 13, 1585–1590 with EcoRI and then inserting the trkA cDNA downstream of the promoter in the 5′ LTR which includes a promoter to drive the expression of the trkA nucleic acid. The ligation mixture was used to transform bacteria, and a clone (pLEN-TrkA) was selected and used for all further experiments. Prior to electroporation pLEN-TrkA was cleaved with NdeI.

Another plasmid was constructed which encodes a truncated TrkA lacking the tyrosine kinase domain. pLEN TrkA was digested with EcoRI and the product run over a 0.8% agarose gel. The 2.7 kb trka insert was then purified using an ISS spin column and ligated overnight at 16° C. to EcoRI digested TA vector. TA-trkA was digested with DraIII and the resultant 4.5 kb and 2 kb bands eluted as above. Non-phosphorylated linkers d(5′CTA GAC TAG TCT ACT TT-3′ (SEQ ID NO:5) and d(3′-ACC GAT GTG ATC AGA TC-5′ (SEQ ID NO:6)) containing a SpeI site and an amber codon were phosphorylated and ligated to the 4.5 Kb and 2 kb bands. The resultant plasmid, TA-trkAΔ was transformed in ONE SHOT cells (Invitrogen, San Diego, Calif.) by heat shock. The 2.2 kb EcoRI trkA fragment from TA-trkAΔ was ligated to EcoRI digested pLEN vector as above. pLEN-trkAΔ was transformed in ONE SHOT cells and the orientation then checked using HindIII, PvuI and SpeI (New England Biolabs, Beverly, Mass.).

The plasmid pLXSN-ET-R which encodes a chimeric receptor was prepared by fusing sequences from the EGF receptor and TrkA cDNA's (Obermeier et al. (1993) *EMBO J.* 12:933–941). Most of the EGF receptor extracellular sequence was derived from a 1680 base pair (bp) XbaI-ApaI restriction fragment. An additional 418 bp at the 3′ end of the larger fragment was derived by PCR. These fragments were ligated and cloned into a Bluescript vector (Stratogene, LaJolla, Calif.). Most of the TrkA intracellular domain was derived from a 1100 bp NarI-EcoRI restriction fragment. The remaining 364 bp were generated by PCR, ligated to the longer fragment via the NarI site and simultaneously cloned into a SmaI/EcoRI-linearized pT7T3 18U vector (Pharmacia, Piscataway, N.J.). These cDNA's were recovered by digestion of the plasmids with XbaI and PvuI, and from the pT7T3 vector by digestion with ScaI and EcoRI. These DNA's were ligated and cloned into a Bluescript plasmid. The insert was then excised and ligated into the pLXSN plasmid, thereby creating the pLXSN-ET-R plasmid.

The preferred vector for inducing expression of TrkA in vivo is a recombinant retrovirus (Kriegler (1990) supra). An advantage of the retrovirus is that it is possible to produce high-titer viral stocks. Since it is desirable to infect as large a percentage as possible of the tumor cells, one needs a very potent stock of virus. In addition, retroviruses infect exclusively proliferating cells (Chiocca et al. (1994) *Virus-mediated Genetic Treatment of Rodent Gliomas* (Wolff, ed.) pp. 245–262, Birkhauser, Boston). In normal adult brain, none of the neurons and very few glial cells are proliferating. A less preferred alternative vector is adenovirus (Stratford-Perricaudet et al. (1994) *Gene Therapy: The Advent of Adenovirus* (Wolff, ed.) pp. 344–362, Birkhauser, N.Y). Although it is possible to prepare high titer stocks of adenoviruses, they lack the specificity of retroviruses. Adenoviruses infect both proliferating and nonproliferating cells and can cause serious toxicity to normal brain tissue (Holzman (1995) *J. Natl. Cancer Inst.* 87:406–410).

To prepare a recombinant retrovirus for expression of TrkA, the vector (for example, pNSV, a Moloney murine leukemia virus vector derived from vector pN2 (Eglitis et al. (1985) *Science* 230:1395–1398) is cut with a specific restriction enzyme, HindIII, downstream of the SV40 promotor (Kriegler, supra). The part of the trkA cDNA coding for the protein is inserted into the vector and ligated. The ligation mix is then used to transfect *Escherichia coli* bacteria. Clones are analyzed for a vector with a trkA insert in the correct orientation. The orientation is checked by restriction enzyme digestion with enzymes that cut within the trkA insert. The appropriate clone is grown up and used to transfect a packaging cell line (PA317). The transfection is carried out using DNA precipitated with calcium phosphate (Chang (1994) *Calcium Phosphate-Mediated DNA Transfection* (Wolff, J. A., ed.), pp. 157–179, Birkhauser, New York). PA317 cells bearing the trkA vector are selected by drug resistance. The vector has a neomycin-resistance nucleic acid, and inclusion of neomycin in the culture medium selects for cells bearing the trkA vector. At this point, the packaging cell line is checked for trkA expression to be certain that the ligation produced the correct virus using immunofluorescence microscopy and a monoclonal antibody specific for TrkA (Ross et al. (1996) *J. Cell Biol.* 132:945–953. The packaging cell line contains nucleic acids that are required for production of infectious virus. Because the resulting infectious virus is defective, it is competent to infect other cell types but produces infectious virus only from the packaging cell lines. Virus in the culture supernatant is collected and used for therapy. Alternatively, the virus-producing cell line can be grafted in the vicinity of the tumor (Chiocca et al., supra). Using either approach the proliferating tumor cells will become infected and express TrkA. Induction of trkA by any other means is also useful in retarding growth of brain tumors.

EXAMPLE 3

Establishment of Transfected Cell Lines $5 \times 10^6$ SH-SY5Y cells were washed once with PBS and harvested using Hank's buffered saline solution (*Meth. Enzymol.* (1979) (Colowick and Kaplan, eds.) 58:119–131) supplemented with 1 mM EDTA. Cells were electroporated in RPMI 1640 with 60 µg NotI linearized pIRVCMV or pIRVCMV-TrkA plasmids (Hempstead et al. (1992) *Neuron* 9:883–896) using a Bio-Rad Gene Pulser (Hercules, Calif.) (450 V, 960 µF, 0.4 cm gap). Cells were seeded onto 25-cm$^2$ tissue Primaria culture flasks (Falcon, Franklin Lakes, N.J.). Selection was performed for 2 weeks using the antibiotic G418 (400 µg/ml in RPMI 1640 and 10% FBS) (Gibco, Gaithersburg, Md. and Sigma Chemicals, St. Louis, Mo.) Multiple clones (>20) of G418-resistant cells were obtained and pooled to create cell lines SY5Y/ET (control vector) and SY5Y/TrkA (expression vector). These lines were maintained at 400 µg/ml in medium containing G418.

LAN5 cells were alternatively electroporated with the pLEN-TrkA or the pLXSN plasmid and selected as described above for SH-SY5Y cells.

To transfect C6 glioma cells, 30–35 µg linearized DNA encoding the growth factor receptor was incubated for 15 minutes on ice and then electroporated at 960 µFd at 0.45 V with infinite resistance. The cells were then resuspended in 10 ml serum supplemented medium and incubated for 48 hours to allow them to recover before selection is initiated in G418 (Gibco). Isolated cells were characterized for the presence of the receptor and maintained under identical conditions as parent cells except for the addition of 300 µg/ml G418 to the medium.

A series of C6 cell lines were transfected with either full length human epidermal growth factor (EGF) or platelet derived growth factor (PDGF) receptors or chimeric receptors consisting of the extracellular component of EGF receptor or PDGF receptor linked to the intracellular tyrosine kinase containing domain of TrkA.

EXAMPLE 4

RT-PCR

Poly (A)$^+$ RNA was prepared using the QuickPrep mRNA Purification Kit (Pharmacia Biotech, Piscataway, N.J. RNA was heat denatured at 95° C. for 5 min and then quickly chilled on ice. Reverse transcriptase buffer, dNTPs, RNase inhibitor and oligo dT (Perkin Elmer GeneAmp RNA PCR kit, Foster City, Calif.) were mixed with 1 µg of poly(A)$^+$ RNA. The reaction was carried out in a thermal cycler (Perkin Elmer 480, Foster City, Calif. 480 using the RT program (15 minutes at 42° C. followed by 5 minutes at 99° C. and cooling to 4° C.). Oligonucleotide primers, buffer and Taq polymerase were then added. Following initial heating of the mixture to 95° C. for 2 minutes, the PCR amplification was carried out for 35 cycles (1 minute at 94° C., 1 minute at 58° C. and 2 minutes at 72° C.) with a final extension of 10 minutes 7 at 72° C. PCR products were then analyzed on a 2% agarose gel and stained for 1 hour with ethidium bromide. The primer sequences assessed and sizes of the predicted PCR products were: trkA: 5'-CGT CAT GGC TGC TTT TAT GG-3' (SEQ ID NO:1); 5'ACT GGC GAG AAG GAG ACA C-3' (SEQ ID NO:2), 75 bp (Wyatt et al. (1993) *Dev.* 119:635–647); low affinity NGF receptor: 5'-CCG ATA CAG TGA CCA CTG TGA TG-3' (SEQ ID NO:3); 5'-AGC AGC CAA GAT GGA GCA ATA GAC-3' (SEQ ID NO:4), 97 bp (Wyatt et al. (1993) *Dev.* 119:635–647).

EXAMPLE 5

Flow Cytometric Analysis

Cells were trypsinized and a trypan blue exclusion test was performed to ensure that >70% of the cells remain viable. $10^6$ cells were then incubated for 2 hours with 10 µg of either TA-1 monoclonal antibody (murine IgG$_3$) or an isotypic IgG$_3$ control monoclonal antibody (Sigma Immunochemicals, St. Louis Mo.). The cells were then washed twice in MEM and resuspended in 1 ml phosphate-buffered saline containing 1 µg fluorescein isothiocyanate-labeled goat anti-mouse antibody (Becton-Dickinson, San Jose Calif.). After two further washes, cells were fixed in 1%. paraformaldehyde and flow cytometric analysis performed on a FACSCAN (BDIS, Mountain View, Calif.). The fluorescence intensity of 10,000 viable cells was measured.

EXAMPLE 6

Western Blotting

Protein was extracted from cells with NP40-containing buffer and centrifuged at 10,000 rpm in microfuge. Protein was then estimated using Sheffield et al.'s solid phase method (Sheffield et al. (1987) *Analyt. Biochem.* 166:49–54). Matched samples were immunoprecipitated with TA-1 monoclonal antibody (1:250 dilution) (Ross et al. (1996) *J. Cell Biol.* 132:945–953) and boiled with β-mercaptoethanol containing buffer. Protein was normalized, using Sheffield et al.'s method (supra). Proteins were separated using polyacrylamide gel electrophoresis on an 8% gel, and Western blotting was then performed using a polyclonal anti-trkA antibody at 1:500 (Clary et al. (1994) *Mol. Biol. Cell* 5:549–563).

EXAMPLE 7

Induction of Cell Cycle Arrest in C6 Cells with Aphidicolin 0.3 µM aphidicolin (Sigma, St. Louis Mo.) was added to logarithmically growing C6 rat glioma cells (ATCC, CCL 107, Rockville, Md.) in MEM medium supplemented with 10% fetal bovine serum (Sigma, St. Louis, Mo.). After 5 days incubation, growth arrested cells were removed with trypsin and $2.0 \times 10^4$ cells were seeded on polyornithine coated coverslips (polyornithine hydrobromide, Sigma) containing aphidicolin supplemented media for another five days in 24-well plates. Coverslips were then fixed in either methanol (10 minutes at $-20°$ C.) or 4% paraformaldehyde (20 minutes at room temperature) for immunohistochemical analysis.

When grown in 10% FBS under routine conditions, C6 cells were flat and polygonal in shape, did not extend long processes, and proliferated very rapidly, as demonstrated by a BrdU uptake in 52% of cells. Less than 5% of cells were stained to any extent with antibodies to GFAP, medium and heavy chain neurofilament (SMI-312) or MAP-2. After adaptation to sublethal concentrations of aphidicolin for 5 days, proliferation was significantly decreased (BrDU labeling 7.2%, $p<0.001$, paired T test). Furthermore, the cells now exhibited a marked change in morphology, with two populations of cells. Approximately one-half (48%) of the cells extended branched complex neurite-like processes ($p<0.0001$, paired T, test compared to standard conditions); the remaining cells appearing epithelioid without visible processes.

After incubation in aphidicolin, clear immunostaining for TrkA protein was noted, especially in the cells with processes. The histochemical character of the cells also changed when grown under these conditions. Cells with processes stained for markers of both astrocytic and neuronal differentiation. Nearly every cell contained staining to some extent for GFAP, cells with processes being particularly intensely stained. Virtually all processed cells were also positive for SMI-312. Since these slides were double stained for GFAP and SMI-312, evidence of coexpression of both markers in the same cell was quite apparent. Such expression of both markers is not artifactual, since no staining was observed when primary antibody was deleted or an isotypic control primary antibody substituted. In addition, many of these cells with processes stained for MAP-2, indicating that more than one neuronal antigen was being expressed.

Coincubation of C6 cells in NGF and aphidicolin resulted in no appreciable changes in immunostaining characteristics, although process length did appear longer.

EXAMPLE 8

MTT Proliferation Assay

Logarithmically growing cells were trypsinized and 20,000 cells in 500 µl medium was added to a 24 well plate which was then incubated for 2 hrs at $37°$ C. The target growth factors were then diluted at the desired concentration in 500 µl medium, added to each well and incubated for 3 to 5 days. Experiments were performed either in MEM supplemented with serum or in a serum-free F12/DMEM (1:1) media supplemented with transferrin and insulin.

At the end of the incubation period, 100 µl MTT ($C_{18}H_{16}N_5SBr$; Sigma, St. Louis, Mo.) solution (5 mg/ml in PBS) was added to each well and incubated for 2 hours at $37°$ C., after which cells are triturated in 1.1 ml isopropanol MTT solubilization solvent solution (Sigma). 300 µl of this mixture was then transferred in duplicate to a 96 well plate and the optical density recorded using a microplate reader at 570/650 $\lambda$. Cell number was then calculated from a standard curve developed by recording O.D.'s from known numbers of similar cells incubated with MTT, solubilized with isopropanol MTT solubilization solution, and prepared in an identical fashion for reading.

EXAMPLE 9

Immunohistochemistry

Coverslips were washed with 1% normal horse serum/ 0.5% Triton-X100 in PBS for 15 minutes. Murine monoclonal antibodies were then applied for specified times and conditions as depicted in Table 2 below. A control murine isotype matched monoclonal antibody diluted in PBS at a concentration equal to the primary antibody was assessed concurrently as a negative control.

After incubation in primary antibody, slides were rinsed x3 in either 1% normal horse serum/0.5% Triton X-100 buffer (murine antibodies) or 1% goat serum/0.5% Triton X-100/PBS for one hour at room temperature. Biotinylated goat anti-rabbit IgG 1:200 (Vector, Burlingame Calif.) was then applied for 30 minutes at room temperature and rinsed for 15 minutes followed by a 30 minute incubation in avidin-conjugated HRP (ABC method, Vectastain, Vector Calif.) and developed in DAB substrate (3,3'-diaminobenzidine 0.7 mg/ml and Urea-$H_2O_2$ 2.0 mg/ml, Sigma FAST tablets, Sigma, St. Louis Mo.) for 5 minutes. Coverslips were then air-dried and mounted (Permount, Fisher Chemicals, N.J.). Samples were viewed with a Zeiss Axioskop microscope Thornwood, N.Y. Micrographs were recorded with Kodak T-MAX 400 film.

TABLE 2

| Ab | Source | Ig Type | Epitope | Type of Cell Recognized | Dilut. Used | Incub. Time |
| --- | --- | --- | --- | --- | --- | --- |
| Rat401 | Pharmingen | murine $IgG_1$ | nestin | undiff. neural cells | 1:500 | 1 hr. |
| SMI312 | Sternberger Monoclonals | murine $IgG_1$ | H- and M-phos chain NFs | neurons | 1:1000 | 1 hr. |
| MAP2 | Boehringer-Mannheim | murine $IgG_1$ | microtubule-assoc. protein | neurons | 1:10 | 1 hr. |
| GFAP | Boehringer-Mannheim | murine $IgG_1$ | GFAP | astrocytes | 1:500 | 1 hr. |
| GFAP | Dako Co. | polyclonal cow | GFAP | astrocytes | 1:10 | 1 hr. |
| GalC | Boehringer-Mannheim | murine $IgG_1$ | galactocerebroside | oligodendrocytes | 1:10 | overnt. |
| TA-1 | Ross Lab | murine $IgG_3$ | trkA | trkA- + cells | 1:250 | overnt. |
| trkA | L Reichardt | polyclonal rabbit | trkA | trkA- + cells | 1:100 | overnt. |

EXAMPLE 10

Soft Agarose Assay

Soft agarose cultures consisted of two layers. The lower layer was prepared by mixing equal volumes of 1.4% (W/V) agarose (SeaPlaque, FMC Bioproducts, Rockland, Me.) and 2×RPMI containing 20% FBS at 37° C. The lower layer was allowed to solidify and upper layer was poured within one hour. The upper layer consisted of equal volume of lower layer mix and cell suspension. Triplicate cultures were set up using 3,000 cells per 60 mm diameter petri dish. Cultures were fed every 5 days with 1 ml of upper layer. After 5 to 6 weeks, cultures were stained with 1 mg/ml of p-iodonitrotetrazolium violet (Sigma, St. Louis, Mo.). Colonies consisting of 20 or more cells were counted after 24 hours. (Small et al. (1987) *Mol. Cell. Biol.* 7:1638–1645).

EXAMPLE 11

Scatter/Motility Assay

An in vitro model of C6 transfectant cell motility was developed which is a modification of the migration assay of Silbergeld (Chicoine et al. (1995) *J. Neurosurg.* 83:665–71; Chicoine et al. (1995) *Neurosurg.* 36:1165–7134; Chicoine et al. (1995) *Cancer* 75:2904–9; and Chicoine et al. (1995) *J. Neurosurg.* 82:615–22). The concept behind this assay is that cells migrate from areas of high to low density as a function of motility.

Near confluent C6 or C6 transfectant tumor cells growing in flasks were treated with 0.5% trypsin for 20 minutes, washed, and $10^5$ cells in 100 µl of MEM medium supplemented with 10% fetal bovine serum were seeded in triplicate onto one pole of a 60 mm Petri dish which was marked in four quadrants and coated with either polyornithine or laminin. This created a confined circular concentration of cells with a radius of 500 µm. After allowing cells to settle on the dish for 1 hour in a humidified flask, the medium was aspirated and the plates washed twice with 5 ml phosphate buffered saline (PBS), after which 5 ml MEM+10% FBS was added and the plates incubated at 37° C. At designated times, medium was aspirated, washed twice with PBS, and fixed at room temperature with 4% paraformaldehyde. Plates were then stained with hematoxylin for 2 minutes prior to examination. The circumferential area traversed in this time was then calculated.

In preliminary studies, C6, $C_6^{trkA}$, and $C6^{trkAA}$ cells were plated in triplicate on polyornithine, and their migration assessed after three days. Even on visual inspection, an obvious difference in the extent of migration was noted between lines. As illustrated in FIG. 7, $C6^{trkA}$ cells migrate significantly less than the other two cell lines after four days (52.5±1.56 mm SEM for $C6^{trkA}$ compared to 72.03±5.78 mm for C6 and 76.67±5.15 for $C6^{trkAA}$, P=0.003, ANOVA on ranks). The number of cell clusters present within 20 mm of the dish center was also significantly less for C6trkA cells (P<0.003, ANOVA on ranks).

Glioma cells under these conditions adhered to the edge of the dish and then started to migrate radially along the edges. After three days, the migration edge appeared as a many cell deep layer of cells that extends from the original droplet along the circumference of the dish. The leading edge of cells was readily ascertained. Using a formula (the angle made by connecting the center with each mark so that it can be multiplied by the circumference/360°), the extent of migration was measured. Additionally, the number of cells migrating to within a specified distance from the center of the dish was counted using a radial grid.

EXAMPLE 12

Intracranial Tumor Implantations

Male Wistar-Kyoto rats (Taconic Farms, Mass.) weighing 200–250 grams were anesthetized with pentobarbital 70 mg/kg i.p. and placed in a stereotactic head holder (David Kopf Instruments, Tujunga, Calif.). A midline incision was made to expose the coronal, sagittal, and lambdoidal sutures and a burr hole made 3 mm lateral and posterior to the bregma. $5\times10^6$ tumor cells in 40 µl of MEM without serum was loaded into a Hamilton syringe which is advanced through the drill hole to a depth of 5 mm. The suspension was then injected over 2 minutes after which the syringe is slowly withdrawn and the skin incision closed with Michel clips. Rats were then assessed daily for signs of illness (lethargy, subconjunctival hemorrhages, gait impairment).

For pathologic studies, preselected animals were perfused with saline and 4% paraformaldehyde via a transcardiac approach after which brains were removed and placed in 0.2 M sodium phosphate buffer containing 30% sucrose. 40 µm sections were cut on a frozen microtome. Tumor extent was initially assessed by staining sections cut through the needle tract with 1% cresyl violet acetate solution, pH 3.8, for 30–60 seconds. Histochemical and immunofluorescent studies were then performed using the methods set forth in Example 9.

EXAMPLE 13

Subcutaneous Implantation of Tumor Cells in Nude Mice

Near confluent glioma cells growing in flasks were treated with 0.5% trypsin for 20 minutes, washed, and resuspended in MEM at a concentration of $1.25\times10^8$ cells/mm$^3$. $5\times10^6$ tumor cells were then injected s.c. into the right flank of male nu/nu Balb/C mice (Taconic Farms). Mice were assessed every other weekday and tumor masses measured in the largest two dimensions. Mice were sacrificed by $CO_2$ inhalation when tumor radii exceed 2 cm.

EXAMPLE 14

Treatment of Malignant Brain Neoplasms

In order to deliver an adequate inoculum of viral particles to a tumor an intratumoral approach is used or particles are infused via a major supplying artery after hyperosmotic opening of the blood brain barrier To accomplish intratumoral inoculation, patients are administered trkA expression vectors via an Ommaya reservoir which will be placed at the time of tumor resection. Patients with either cystic tumors or those in which a subtotal or total resection can be accomplished are eligible for this form of vector delivery. During the immediate postoperative period and at monthly intervals afterward, patients are administered $10^7$–$10^{10}$ plate forming units (PFU), and preferably $10^8$–$10^9$ PFU of trkA expression vector in 2–3 ml of sterile bacteriostatic PBS. This is done with the patient awake in supine position using conventional sterile techniques. Monthly infusions continue until radiographic tumor progression or treatment complications occur.

An alternative mode of delivery is via an intraarterial approach with blood brain barrier opening with hyperosmotic mannitol. Such a procedure is performed initially one week post-surgery. Patients whose tumors are supplied primarily by one of the major carotid or basilar artery are brought to the Angiography suite and a routine catheterization of the cerebral artery supplying the major tumor territory performed. After this is accomplished, hyperosmotic (1.6 M) mannitol is infused at a rate of 5 ml/min over 20–30 minutes. This results in a reversible opening of the blood brain barrier which lasts for several minutes after the infusion is completed. During this time, $10^8$–$10^9$ PFUs of trkA expression vector diluted in 50 ml sterile normal saline is infused at a rate of 5–10 ml/min. At the completion of the infusion, the catheter is removed. The procedure is repeated every month until radiographic tumor progression or treatment complications occur.

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. A method of treating a neurological tumor in a mammal, the method comprising:
   (a) providing a vector comprising a first nucleic acid encoding an intracellular domain of a tyrosine kinase receptor for a neurotrophin and a second nucleic acid encoding an extracellular domain of a tyrosine kinase receptor, wherein the second nucleic acid is in operative association with the first nucleic acid; and
   (b) administering to the mammal a therapeutically effective amount of a pharmaceutical composition comprising the vector and a physiologically acceptable carrier, wherein the nucleic acids encoding the intracellular domain of the receptor and the extracellular domain of the receptor are expressed in the tumor.

2. The method of claim 1, wherein the tumor is selected from the group consisting of a neuroblastoma, a glioma, an astrocytoma, and a glioblastoma.

3. The method of claim 1, wherein the first nucleic acid encodes a receptor for a neurotrophin factor selected from the group consisting of nerve growth factor, neurotrophin-3, neurotrophin-4, and brain derived neurotrophic factor.

4. The method of claim 1, wherein the receptor is selected from the group consisting of TrkA, TrkB, and TrkC.

5. The method of claim 1, wherein the receptor tyrosine kinase is cognate for a differentiation factor selected from the group consisting of a neurotrophin, an interleukin, epidermal growth factor, platelet derived growth factor, a fibroblast growth factor, insulin, insulin-like growth factor, and macrophage colony stimulating factor.

6. The method of claim 1 wherein the pharmaceutical composition is administered to the tumor by intravenous injection or intratumoral inoculation.

7. The method of claim 5, wherein the differentiation factor is a neurotrophin.

8. The method of claim 5, wherein the differentiation factor is epidermal growth factor.

9. The method of claim 5, wherein the differentiation factor is platelet derived growth factor.

10. The method of claim 7, wherein the neurotrophin is selected from the group consisting of nerve growth factor, brain derived growth factor, and neurotrophin-3.

11. The method of claim 10, wherein the neurotrophin is nerve growth factor.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:1:

CGTCATGGCT GCTTTTATGG          20

(2) INFORMATION FOR SEQ ID NO:2:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:2:

ACTGGCGAGA AGGAGACAC          19

(2) INFORMATION FOR SEQ ID NO:3:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:3:

CCGATACAGT GACCACTGTG ATG       23

(2) INFORMATION FOR SEQ ID NO:4:

-continued (i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:4:

AGCAGCCAAG ATGGAGCAAT AGAC                                          24

(2) INFORMATION FOR SEQ ID NO:5:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:5:

CTAGACTAGT CTACTTT                                                  17

(2) INFORMATION FOR SEQ ID NO:6:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:6:

ACCGATGTGA TCAGATC                                                  17